United States Patent
Oh et al.

(10) Patent No.: US 12,256,986 B2
(45) Date of Patent: Mar. 25, 2025

(54) SYSTEMS AND METHODS FOR DETECTING LEAKAGE CURRENTS IN HIGH-FREQUENCY ABLATION SYSTEMS

(71) Applicant: Advanced Neuromodulation Systems, Inc., Plano, TX (US)

(72) Inventors: Seil Oh, Dallas, TX (US); Binesh Balasingh, Prosper, TX (US); William Winstrom, Leander, TX (US); Simran Singh, Richardson, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 618 days.

(21) Appl. No.: 17/378,597

(22) Filed: Jul. 16, 2021

(65) Prior Publication Data

US 2022/0183753 A1     Jun. 16, 2022

Related U.S. Application Data

(60) Provisional application No. 63/126,288, filed on Dec. 16, 2020.

(51) Int. Cl.
*A61B 18/16* (2006.01)
*A61B 18/12* (2006.01)
*A61B 18/00* (2006.01)

(52) U.S. Cl.
CPC .......... *A61B 18/16* (2013.01); *A61B 18/1206* (2013.01); *A61B 2018/00577* (2013.01)

(58) Field of Classification Search
CPC .. A61B 18/16; A61B 18/1206; A61B 18/1233
See application file for complete search history.

(56) References Cited

U.S. PATENT DOCUMENTS

| | | | |
|---|---|---|---|
| 7,736,357 B2 | 6/2010 | Lee, Jr. et al. | |
| 8,560,062 B2 | 10/2013 | Rittman, III et al. | |
| 10,342,606 B2 | 7/2019 | Cosman et al. | |
| 2013/0197510 A1* | 8/2013 | Heckel | A61B 18/1206 606/41 |
| 2016/0081740 A1* | 3/2016 | Heckel | A61B 18/1233 606/34 |

* cited by examiner

*Primary Examiner* — Michael F Peffley
*Assistant Examiner* — Samantha M Good
(74) *Attorney, Agent, or Firm* — Norton Rose Fulbright US LLP

(57) ABSTRACT

The present disclosure provides systems and methods for detecting leakage currents in radio-frequency (RF) ablation systems. An RF generator may be configured to disable an electrical return path from a patient to a ground terminal. The RF generator may also be configured to apply an electrical signal to an electrode that is positioned to be in proximity to target tissue of the patient. The RF generator may be further configured to measure a leakage impedance while the electrical return path is disabled and the electrical signal is applied to the electrode. The RF generator may also be configured to control RF ablation therapy based, at least in part, on the measured leakage impedance. Other features are also claimed and described.

8 Claims, 4 Drawing Sheets

SYSTEMS AND METHODS FOR DETECTING LEAKAGE CURRENTS IN HIGH-FREQUENCY ABLATION SYSTEMS

CROSS-REFERENCE TO RELATED APPLICATIONS

The present application claims the benefit of U.S. Provisional Application No. 63/126,288, filed Dec. 16, 2020 and entitled "SYSTEMS AND METHODS FOR DETECTING LEAKAGE CURRENTS IN HIGH-FREQUENCY ABLATION SYSTEMS," the disclosure of which is incorporated by reference herein in its entirety.

FIELD OF THE DISCLOSURE

The present disclosure relates generally to high-frequency ablation systems, and more particularly to techniques for detecting leakage currents in radio-frequency (RF) ablation systems. Certain aspects of the technology discussed below can enable and provide enhanced features and techniques for RF ablation systems, including better patient safety, better RF power delivery, and lower cost.

BACKGROUND OF THE DISCLOSURE

RF ablation may be used to treat numerous health conditions. For example, RF ablation may be used to treat tumors, arrhythmia, skin conditions, and chronic pain.

Typically, RF ablation causes the destruction and/or removal of biological tissue. In particular, during an RF ablation procedure, RF energy may be used to generate heat that is then used to ablate biological tissue targeted by the RF ablation procedure. An RF generator is typically used to generate the RF energy and the heat by causing a current to flow from an active electrode to a neutral electrode, where both the active electrode and the neutral electrode are disposed in proximity (e.g., adjacent) to tissue to be ablated (e.g., the electrodes may be positioned within the body of a patient using one or more cannulas to access a target site). Ideally, all of the electrical current from the RF generator should flow from the active electrode to the neutral electrode.

Due to non-ideal conditions in RF ablation systems, not all of the electrical current from an RF generator will likely flow from the active electrode to the neutral electrode. For example, due to at least the electrical network presented by the patient, poor isolation of the patient from ground (earth), and parasitics associated with an RF ablation system, a leakage current path can be created. The leakage current can allow for the flow of excessive amounts of unintended current that can cause thermal burns.

Conventional techniques for addressing leakage current in RF ablation systems are less than optimal and have significant drawbacks. For example, simulation tools tend to be inaccurate at high-frequency operating conditions and for very complex hardware systems, making them unreliable for accurate simulation of RF ablation systems. As a result, leakage current is often addressed after a hardware verification phase, typically requiring complete hardware redesign of the RF ablation system.

BRIEF SUMMARY OF THE DISCLOSURE

The following summarizes some aspects of the present disclosure to provide a basic understanding of the discussed technology. This summary is not an extensive overview of all contemplated features of the disclosure and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

The present disclosure provides radio-frequency (RF) ablation systems and methods for detecting leakage currents in RF ablation systems and for allowing the detected leakage currents to be addressed without complete redesign of the hardware of the RF ablation systems. In some embodiments, an RF ablation system may control switches within the RF ablation system to aid the detection of leakage currents. According to some embodiments, if an excessive amount of leakage current is detected, the RF ablation system may regulate the RF power to control the leakage or abort RF ablation therapy so that a clinician can take appropriate actions to address the detected leakage current.

In one embodiment, the present disclosure is directed to a method for controlling a RF ablation system. The method includes disabling an electrical return path from a patient to a ground terminal. The method also includes applying an electrical signal to an electrode that is positioned to be in proximity to target tissue of the patient. The method further includes measuring a leakage impedance while the electrical return path is disabled and the electrical signal is applied to the electrode. The method also includes controlling RF ablation therapy based, at least in part, on the measured leakage impedance.

In another embodiment, the present disclosure is directed to an RF ablation system. The RF ablation system includes a first switch in an electrical source path and configured to couple an electrical source to an electrode. The RF ablation system further includes a second switch in an electrical return path and configured to couple a patient to a ground terminal. The RF ablation system also includes at least one processor coupled to the first switch and the second switch. The at least one processor can be configured to disable the second switch to disable the electrical return path from the patient to the ground terminal. The at least one processor can also be configured to enable the first switch to apply an electrical signal to the electrode that is positioned to be in proximity to target tissue of the patient. The at least one processor can be further configured to measure a leakage impedance while the electrical return path is disabled and the electrical signal is applied to the electrode. The at least one processor can also be configured to control RF ablation therapy based, at least in part, on the measured leakage impedance.

In another embodiment, the present disclosure is directed to an RF ablation system. The RF ablation system includes a cannula configured to include an electrode. The RF ablation system also includes an RF generator coupled to the at least one cannula. The RF generator can be configured to disable an electrical return path from a patient to a ground terminal. The RF generator can also be configured to apply an electrical signal to the electrode that is positioned to be in proximity to target tissue of the patient. The RF generator can be further configured to measure a leakage impedance while the electrical return path is disabled and the electrical signal is applied to the electrode. The RF generator can also be configured to control RF ablation therapy based, at least in part, on the measured leakage impedance.

Other aspects, features, and embodiments will become apparent to those of ordinary skill in the art, upon reviewing the following description of specific, exemplary embodiments in conjunction with the accompanying figures. While features may be discussed relative to certain aspects and figures below, all embodiments can include one or more of the advantageous features discussed herein. In other words, while one or more aspects may be discussed as having certain advantageous features, one or more of such features may also be used in accordance with the various aspects. In similar fashion, while exemplary aspects may be discussed below as device, system, or method aspects, the exemplary aspects can be implemented in various devices, systems, and methods.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following the reference label with a second label that distinguishes among the similar components. If just the first reference label is used in the specification, the description is applicable to any one of the similar components having the same first reference label irrespective of the second reference label.

DETAILED DESCRIPTION OF THE DISCLOSURE

The detailed description set forth below, in connection with the appended drawings, is intended as a description of various configurations and is not intended to limit the scope of the disclosure. Rather, the detailed description includes specific details for the purpose of providing a thorough understanding of the inventive subject matter. It will be apparent to those skilled in the art that these specific details are not required in every case and that, in some instances, well-known structures and components are shown in block diagram form for clarity of presentation.

The present disclosure provides systems and methods for detecting leakage currents in radio-frequency (RF) ablation systems and for allowing the detected leakage currents to be addressed without complete redesign of the hardware of the RF ablation systems. In some embodiments, an RF ablation system may control switches within the RF ablation system to aid the detection of leakage currents. According to some embodiments, if an excessive amount of leakage current is detected, the RF ablation system may regulate the RF power to control the leakage or abort RF ablation therapy so that a clinician can take appropriate actions to address the detected leakage current.

Figure 1:
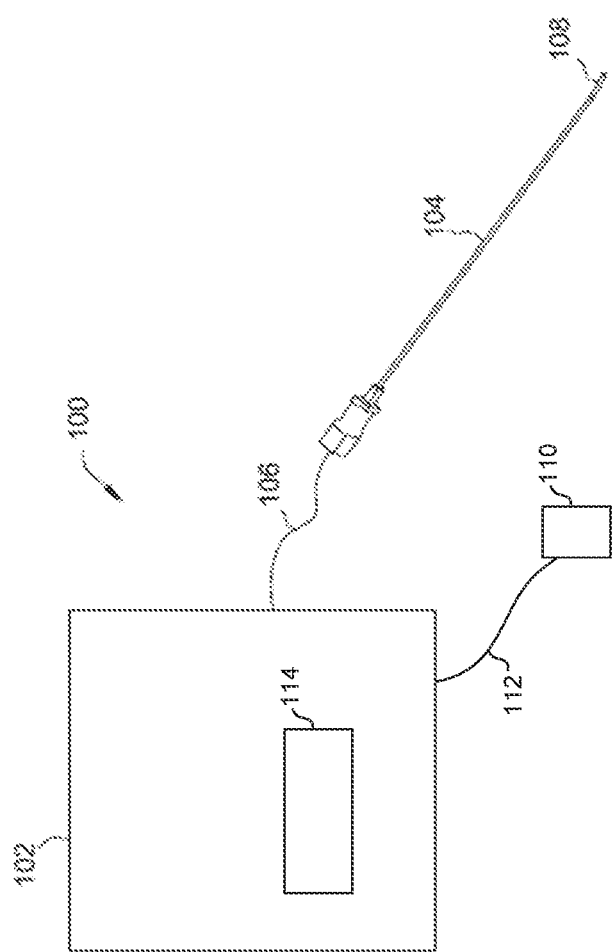
FIG. 1 is a schematic view of a radio-frequency (RF) ablation system according to some embodiments of the present disclosure.

FIG. 1, as an example, shows a schematic view of a radio-frequency (RF) ablation system according to some embodiments of the present disclosure. RF ablation system 100 includes an RF generator 102 coupled to a cannula 104 via a cable 106. According to some embodiments, the pair of components that include cannula 104 and cable 106 may represent, e.g., include, one or more pairs of cannulas and cables that are coupled to RF generator 102. For example, in some embodiments, one or more pairs of cannulas and cables may be coupled to RF generator 102 in parallel to each other. In some embodiments, during operation, RF generator 102 may control energy delivered to a patient through a tip electrode 108 of cannula 104. For example, RF generator 102 may cause current to be passed through an active electrode, such as the tip electrode 108 of cannula 104. According to some embodiments, the current passed through the active electrode may pass through a patient and to a neutral electrode 110. In additional embodiments, the current may return to RF generator 102 from neutral electrode 110 via another cable 112. RF generator 102 may include a processor 114. In some embodiments, processor 114 may represent, e.g., include, one or more processors of RF generator 102. According to some embodiments, processor 114 may control various components within RF generator 102 to cause RF generator 102 to perform various operations, such as one or more of the operations disclosed herein as being performed by RF generator 102.

Figure 2:
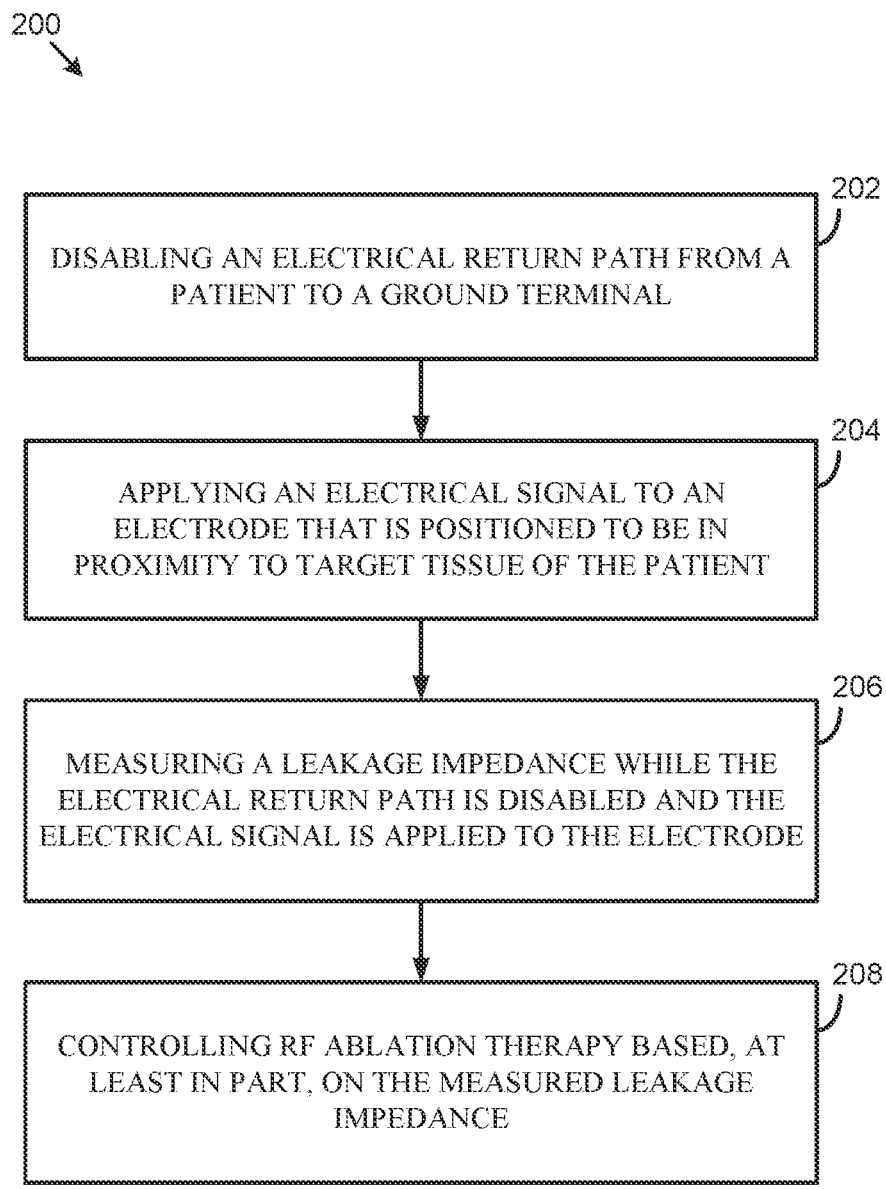
FIG. 2 is a block diagram illustrating a method for detecting leakage currents in RF ablation systems according to some embodiments of the present disclosure.

FIG. 2, as an example, shows a block diagram illustrating a method for detecting leakage currents in RF ablation systems according to some embodiments of the present disclosure. Aspects of method 200 may be implemented with various other embodiments of this disclosure described with respect to FIGS. 1 and 3-4, such as RF ablation system 100, or more specifically RF generator 102. For example, RF generator 102, or at least one processor of an RF generator, such as processor 114, may perform method 200.

FIG. 2 illustrates a method 200 that may be performed by an RF ablation system, such as RF ablation system 100, or more specifically an RF generator, such as RF generator 102, or a processor of an RF generator, such as processor 114. At block 202, an RF generator, such as RF generator 102, or a processor of an RF generator, such as processor 114, may disable an electrical return path from a patient to a ground terminal, as described in more detail below. Method 200 also includes, at block 204, an RF generator, or a processor of an RF generator, applying an electrical signal to an electrode that is positioned to be in proximity to target tissue of the patient, as described in more detail below. At block 206, method 200 further includes an RF generator, or a processor of an RF generator, measuring a leakage impedance while the electrical return path is disabled and the electrical signal is applied to the electrode, as described in more detail below. Method 200 also includes, at block 208, an RF generator, or a processor of an RF generator, controlling RF ablation therapy based, at least in part, on the measured leakage impedance.

In some embodiments, the actions shown at blocks 202 through 208 of method 200 may be a subset of the overall operations performed by an RF generator to detect leakage currents, control RF ablation therapy, and allow the detected leakage currents to be addressed. The relationship between the actions shown at blocks 202 through 208 of method 200 and other operations that are performed by an RF generator to detect leakage currents, control RF ablation therapy, and allow the detected leakage currents to be addressed may become more evident from a discussion of the overall operations performed by an RF generator to detect leakage currents, control RF ablation therapy, and allow the detected leakage currents to be addressed.

Figure 3:
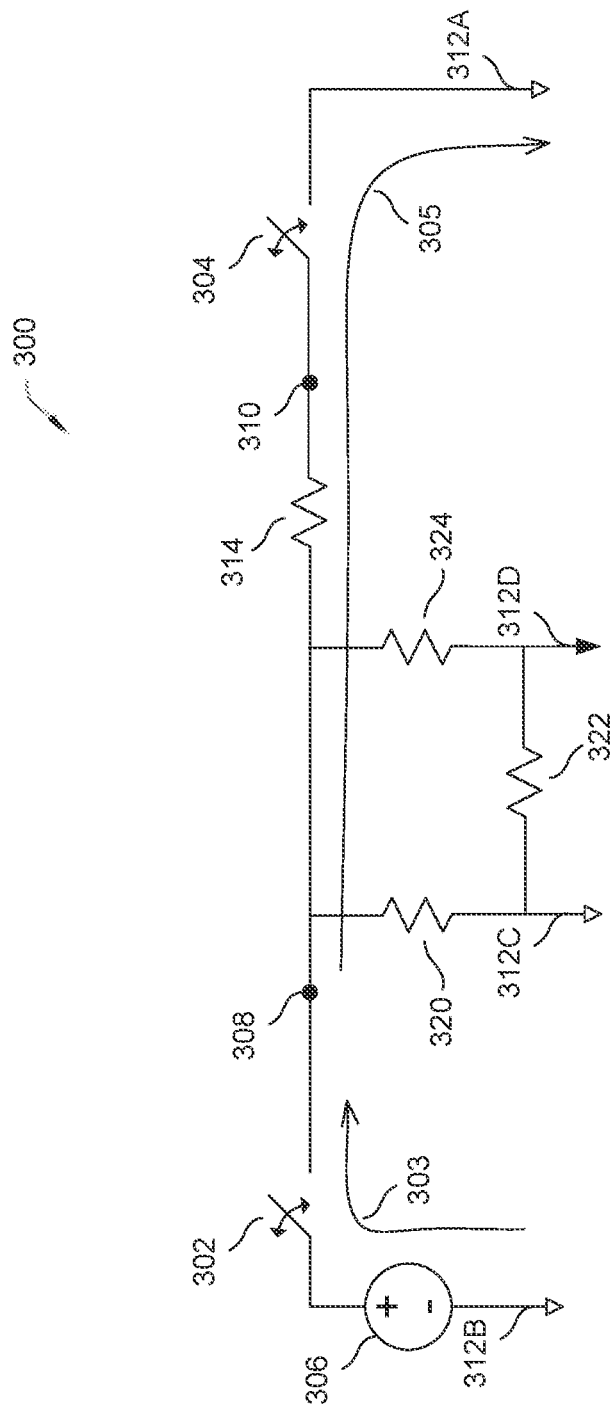
FIG. 3 is a circuit diagram of an RF ablation system according to some embodiments of the present disclosure.

FIG. 3, as an example, shows a circuit diagram of an RF ablation system according to some embodiments of the present disclosure. In some embodiments, circuit diagram 300 may illustrate additional features and components of an RF ablation system, such as RF ablation system 100, and/or additional features and components of an RF generator, such as RF generator 102. In circuit diagram 300, there is a first switch 302 and a second switch 304. In some embodiments, each of the first switch 302 and the second switch 304 may independently represent, e.g., independently include, one or more switches and/or relays. A switch and/or relay may be electrical and/or mechanical. According to some embodiments, at least one processor of an RF generator, such as processor 114 of RF generator 102 illustrated in FIG. 1, may be electrically coupled to the first switch 302 and/or the second switch 304 to control the first switch 302 and/or the second switch 304 to perform operations disclosed herein.

As illustrated in FIG. 3, the first switch 302 may be located in an electrical source path 303. In some embodiments, the electrical source path 303 may refer to an intended electrical path between an electrical source, such as electrical source 306 illustrated in FIG. 3, and an active electrode 308, also referred to herein as electrical node 308. According to some embodiments, electrical source 306 may refer to an RF electrical source, such as an RF voltage source and/or an RF current source. In additional embodiments, active electrode 308 may refer to an electrode located at a tip of a cannula, such as tip electrode 108 of cannula 104 illustrated in FIG. 1. Accordingly, in some embodiments, first switch 302 may be configured to couple an electrical source, such as electrical source 306, to an electrode located at electrical node 308, such as tip electrode 108 of cannula 104 via cable 106. In some aspects, the electrical source 306 and the first switch 302 may both be located within an RF generator, such as RF generator 102, and may be coupled to the active electrode 308, such as tip electrode 108 of cannula 104, via a cable, such as cable 106.

As illustrated in FIG. 3, the second switch 304 may be located in an electrical return path 305. In some embodiments, the electrical return path 305 may refer to an intended electrical return path 305 for current to flow from the active electrode 308, through intended biological tissue of a patient, through a neutral electrode 310, also referred to herein as electrical node 310, and to a ground terminal, such as ground terminal 312A illustrated in FIG. 3. The intended biological tissue of a patient through which current is intended to flow during RF ablation therapy is illustrated in circuit diagram 300 with ablation impedance 314. In some embodiments, ablation impedance 314 may not represent a physical component of an RF ablation system. Instead, ablation impedance 314 may represent the biological tissue in proximity to the electrodes that completes the electrical circuit shown in FIG. 3. According to some embodiments, ground terminal 312 may refer to a neutral ground terminal and/or an earth ground terminal. In additional embodiments, neutral electrode 310 may refer to a neutral electrode that is coupled to a patient, such as neutral electrode 110 illustrated in FIG. 1. Accordingly, in some embodiments, second switch 304 may be configured to couple a ground terminal, such as ground terminal 312, to a patient, e.g., to a patient associated with ablation impedance 314 and coupled to neutral electrode 310, such as neutral electrode 110. In some aspects, second switch 304 and a ground terminal, such as ground terminal 312A, may both be located within an RF generator, such as RF generator 102, and may be coupled to the neutral electrode 310 via a cable, such as cable 112.

In some embodiments, an RF generator, such as RF generator 102, or at least one processor of an RF generator, such as processor 114 illustrated in FIG. 1, may be configured to control one or more of the components illustrated in circuit diagram 300 to perform operations disclosed herein, such as to detect leakage currents, control RF ablation therapy, and allow the detected leakage currents to be addressed. For example, in some embodiments, RF generator 102, or processor 114 of RF generator 102, may be configured to disable the second switch 304. According to some embodiments, a switch may be disabled by deactivating or opening the switch. In some embodiments, the second switch 304 may be disabled to disable the electrical return path 305 from the patient, e.g., represented by ablation impedance 314, to a ground terminal 312A, e.g., as shown at block 202 of FIG. 2.

According to some embodiments, RF generator 102, or processor 114 of RF generator 102, may also be configured to enable the first switch 302. In some embodiments, a switch may be enabled by activating or closing the switch. According to some embodiments, the first switch 302 may be enabled to apply an electrical signal to the active electrode 308, such as an electrode at a tip of a cannula, that is positioned to be in proximity to target tissue of the patient, e.g., as shown at block 204 of FIG. 2. In some embodiments, target tissue of the patient may be tissue that is intended to be ablated by the RF ablation system. According to some embodiments, the electrode being positioned to be in proximity to target tissue of the patient may include the electrode being positioned within the body of the patient using one or more cannulas to access the target tissue. In additional embodiments, the electrode being positioned to be in proximity to target tissue of the patient may include the electrode being positioned adjacent to the target tissue. According to some embodiments, the electrode may be positioned near an ablation site and may be at least partially within the patient. For example, at least the tip of the cannula that includes the electrode may be positioned within the patient.

In some embodiments, the electrical signal applied to the active electrode 308 by an RF generator 102, or processor 114 of RF generator 102, may refer to an RF electrical signal, such as an RF voltage and/or an RF current. According to some embodiments, the voltage and/or current of the electrical signal may be the same as a voltage and/or current used during RF ablation therapy to ablate target tissue. In additional embodiments, the voltage and/or current of the electrical signal may not be the same as a voltage and/or current used during RF ablation therapy to ablate target tissue. According to some embodiments, the power of the electrical signal may be the same as a power of a signal used during RF ablation therapy to ablate target tissue. In additional embodiments, the power of the electrical signal may not be the same as a power of a signal used during RF ablation therapy to ablate target tissue. According to some embodiments, the electrical signal may be applied for various amounts of time. For example, in some embodiments, the electrical signal may be applied at least until the leakage impedance or leakage current is determined. In some embodiments, the electrical signal may be applied at a constant frequency. In additional embodiments, the electrical signal may be applied at different frequencies, e.g., a range of frequencies may be swept to apply the electrical signal to the active electrode 308.

In some embodiments, an RF generator 102, or processor 114 of RF generator 102, may be further configured to measure a leakage impedance and/or a leakage current while the electrical return path 305 is disabled and an electrical signal is applied to the active electrode 308, such as an electrode located at a tip of a cannula, e.g., as shown at block 206 of FIG. 2. According to some embodiments, the electrical signal may be applied to the electrode while the electrical source path 303 is enabled. For example, an RF voltage may be applied to active electrode 308 such that RF current may flow if there is a path for current flow in circuit 300. Ideally, no current should flow from electrical source 306 through circuit 300 when the electrical return path 305 is disabled. However, because of non-ideal conditions in RF ablation systems, current may still flow even when the electrical return path 305 is disabled. Such current may be referred to as leakage current. Accordingly, in some embodiments, leakage current may include current that flows in the RF ablation system 300 when the electrical return path 305 is disabled. Similarly, leakage impedance may include impedance observed by electrical source 306 of the RF ablation system 300 when the electrical return path 305 is disabled.

According to some embodiments, there may be leakage paths present in circuit diagram 300 through which current may leak when the electrical return path 305 is disabled. In FIG. 3, a few leakage paths are illustrated with impedances 320, 322, and 324. In some embodiments, impedances 320, 322, and/or 324 may represent physical components of an RF ablation system. According to additional embodiments, impedances 320, 322, and/or 324 may not represent physical components of an RF ablation system. Instead, impedances 320, 322, and/or 324 may represent the impedances of various parasitic paths or other current paths present in the environment in which the RF ablation system is disposed. For example, even when electrical return path 305 is disabled, current may still leak through one or more of impedances 320, 322, and/or 324. In some embodiments, impedance 320 may represent leakage current through active electrode 308, such as an electrode located at a tip of a cannula, to a neutral ground terminal 312C, impedance 322 may represent leakage current that flows between a neutral ground terminal 312C and an earth ground terminal 312D, and impedance 324 may represent leakage current through active electrode 308, such as an electrode located at a tip of a cannula, to an earth ground terminal 312D.

In some embodiments, leakage current within an RF ablation system 300 and leakage impedance of the RF ablation system 300 may be related to each other. For example, because of the general voltage=impedance*current relationship between voltage, impedance, and current, once the total leakage impedance is determined, the total leakage current may be approximated by dividing the voltage applied by the electrical source 306 by the determined leakage impedance. Similarly, the total leakage impedance may be approximated by dividing the voltage applied by the electrical source 306 by the determined leakage current. In FIG. 3, the total leakage impedance may be measured from the total leakage current. For example, the total leakage impedance may be determined by applying a voltage to active electrode 308, e.g., as shown at block 204 of FIG. 2, while the electrical return path 305 is disabled and measuring the total current that flows from the electrical source 306. That resulting current may be the leakage current, and the total leakage impedance may be determined by dividing that leakage current from the voltage applied to active electrode 308 by electrical source 306.

Figures 4A, 4B:
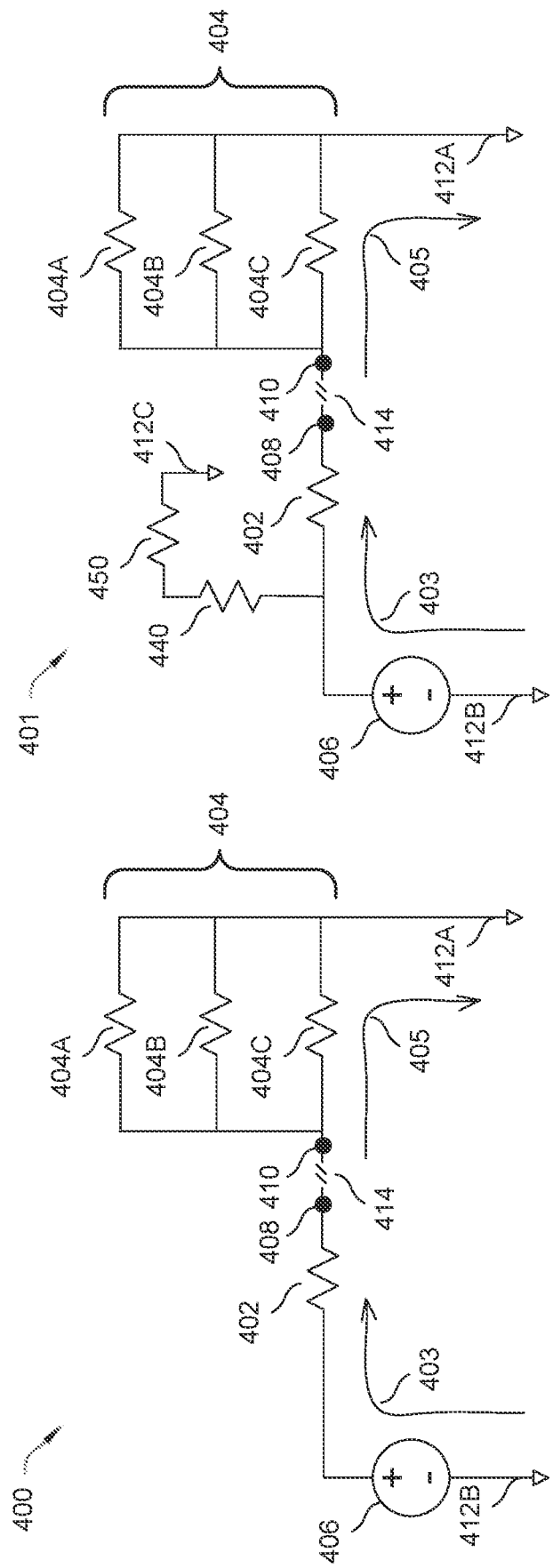
FIGS. 4A and 4B are other example circuit diagrams of an RF ablation system according to some embodiments of the present disclosure.

FIGS. 4A and 4B are other example circuit diagrams of an RF ablation system according to some embodiments of the present disclosure. In some embodiments, circuit diagrams 400 and 401 may each illustrate additional features and components of an RF ablation system, such as RF ablation system 100, and/or additional features and components of an RF generator, such as RF generator 102. In FIGS. 4A and 4B, some switches, such as first switch 402 and second switches 404A, 404B, and 404C, are illustrated with impedances that represent their respective closed-switch or open-switch impedances. In comparison to FIG. 3, whereas in FIG. 3 the switches 302 and 304 are illustrated in such a way as to show how the switches function to enable or disable different sections of the circuit 300, in FIGS. 4A and 4B the switches 402, 404A, 404B, and 404C are illustrated as impedances to illustrate the impedance characteristics of the switches when they are in an open state, e.g., disabled, or a closed state, e.g., enabled. Also, in comparison with FIG. 3, FIG. 4B also models leakage current paths different than in FIG. 3 to show that leakage paths may manifest themselves in various ways and can be modeled in various ways, with FIGS. 3 and 4B showing only two of many different ways that leakage paths can be modeled. Nonetheless, regardless of how leakage paths actually manifest themselves, a common scheme, such as a scheme of this disclosure, may be used to detect leakage current, as previously described for FIG. 3 and described below for FIG. 4B. A person of ordinary skill in the art would readily recognize that the schemes described in this disclosure for detecting leakage current may also be applied to other circuits that show different leakage current path manifestations than those shown in FIGS. 3 and 4B.

Now turning more specifically to the details illustrated in FIGS. 4A and 4B, in circuit diagrams 400 and 401, the first switch 402 is enabled, i.e., closed or activated, and the second switch 404 is disabled, i.e., deactivated or open. In some embodiments, each of the first switch 402 and the second switch 404 may independently represent, e.g., independently include, one or more switches and/or relays. For example, circuit diagrams 400 and 401 show second switch 404 including three different switches 404A, 404B, and 404C in parallel. In some embodiments, each of the switches 402, 404A, 404B, and 404C may be associated with a different channel of an RF generator. As described previously, in FIGS. 4A and 4B, the switches, e.g., first switch 402 and second switches 404A, 404B, and 404C, are illustrated with impedances that represent their respective closed-switch or open-switch impedances. As one example, if each switch 404A, 404B, and 404C has an open-switch impedance of 2000 Ohms, then the impedances 404A, 404B, and 404C illustrated in FIGS. 4A and 4B may each represent 2000 Ohms. Similarly, if switch 402 has a closed-switch impedance of 120 Ohms, then the impedance 402 illustrated in FIGS. 4A and 4B may represent 120 Ohms. According to some embodiments, at least one processor of an RF generator, such as processor 114 of RF generator 102 illustrated in FIG. 1, may be electrically coupled to the first switch 402 and/or the second switch 404 to control the first switch 402 and/or the second switch 404 to perform operations disclosed herein.

As illustrated in FIGS. 4A and 4B, the first switch 402 may be located in an electrical source path 403. In some embodiments, the electrical source path 403 may refer to an intended electrical path between an electrical source, such as electrical source 406 illustrated in FIGS. 4A and 4B, and an active electrode 408, also referred to herein as electrical node 408. In additional embodiments, active electrode 408 may refer to an electrode located at a tip of a cannula, such as tip electrode 108 of cannula 104 illustrated in FIG. 1. In some embodiments, the electrical source 406 and the first switch 402 may both be located within an RF generator, such as RF generator 102, and may be coupled to the active electrode 408, such as tip electrode 108 of cannula 104, via a cable, such as cable 106.

As illustrated in FIGS. 4A and 4B, the second switch 404 may be located in an electrical return path 405. In some embodiments, the electrical return path 405 may refer to an intended electrical return path 405 for current to flow from the active electrode 408, through intended biological tissue of a patient, through a neutral electrode 410, also referred to herein as electrical node 410, and to a ground terminal, such as ground terminal 412A illustrated in FIGS. 4A and 4B. The intended biological tissue of a patient through which current is intended to flow during RF ablation therapy is illustrated in circuit diagrams 400 and 401 with section 414 of circuit diagrams 400 and 401. In additional embodiments, neutral electrode 410 may refer to a neutral electrode that is coupled to a patient, such as neutral electrode 110 illustrated in FIG. 1. In some embodiments, second switch 404 and a ground terminal, such as ground terminal 412A, may both be located within an RF generator, such as RF generator 102, and may be coupled to the neutral electrode 410 via a cable, such as cable 112.

In some embodiments, an RF generator, such as RF generator 102, or at least one processor of an RF generator, such as processor 114 illustrated in FIG. 1, may be configured to control one or more of the components illustrated in circuit diagrams 400 and 401 to perform operations disclosed herein, such as to detect leakage currents, control RF ablation therapy, and allow the detected leakage currents to be addressed. For example, in some embodiments, RF generator 102, or processor 114 of RF generator 102, may be configured to disable the second switch 404, which includes three switches 404A, 404B, and 404C in parallel. In some embodiments, the second switch 404 may be disabled to disable the electrical return path 405 from the patient, e.g., located at section 414, to a ground terminal 412A, e.g., as shown at block 202 of FIG. 2.

According to some embodiments, RF generator 102, or processor 114 of RF generator 102, may also be configured to enable the first switch 402. According to some embodiments, the first switch 402 may be enabled to apply an electrical signal to the active electrode 408, such as an electrode at a tip of a cannula, that is positioned to be in proximity to target tissue of the patient, e.g., as shown at block 204 of FIG. 2. According to some embodiments, the electrode may be positioned near an ablation site and may be at least partially within the patient. For example, at least the tip of the cannula that includes the electrode may be positioned within the patient.

In some embodiments, an RF generator 102, or processor 114 of RF generator 102, may be further configured to measure a leakage impedance and/or a leakage current while the electrical return path 405 is disabled and an electrical signal is applied to the active electrode 408, such as an electrode located at a tip of a cannula, e.g., as shown at block 206 of FIG. 2. According to some embodiments, the electrical signal may be applied to the electrode while the electrical source path 403 is enabled. For example, a voltage may be applied to active electrode 408 such that current may flow if there is a path for current flow in circuits 400 and 401. In FIG. 4B, a leakage path is illustrated with impedances 440 and 450. For example, even when electrical return path 405 is disabled, current may still leak through one or more of impedances 440 and 450. In some embodiments, impedance 440 may represent leakage current through biological tissue of a patient that is not target tissue for the RF ablation therapy, e.g., unintended biological tissue, and impedance 450 may represent leakage current from the unintended biological tissue to a ground terminal 412C. One of skill will readily understand that the location of the leakage path illustrated in FIG. 4B is simply for illustration purposes because it is generally understood that there may be many different leakage paths throughout an RF ablation system. In other words, the leakage path illustrated in FIG. 4B is only an example leakage path included in FIG. 4B simply to show the existence of leakage in circuit diagram 401, but is not exhaustive of all leakage paths in circuit diagram 401. FIG. 4A does not show the leakage paths shown in FIG. 4B. In FIG. 4B, the total leakage impedance may be measured from the total leakage current. For example, the total leakage impedance may be determined by applying a voltage to active electrode 408, e.g., as shown at block 204 of FIG. 2, while the electrical return path 405 is disabled and measuring the total current that flows from the electrical source 406. That resulting current may be the leakage current, and the total leakage impedance may be determined by dividing that leakage current from the voltage applied to active electrode 408 by electrical source 406.

In some embodiments, an RF generator 102, or processor 114 of RF generator 102, may be further configured to control RF ablation therapy based, at least in part, on the measured leakage impedance, e.g., as shown at block 208 of FIG. 2. According to some embodiments, the RF ablation therapy may refer to RF ablation therapy that is applied to a patient, e.g., a patient represented by ablation impedance 314 in FIG. 3 or section 414 in FIGS. 4A and 4B.

According to some embodiments, an RF generator 102, or processor 114 of RF generator 102, controlling RF ablation therapy based, at least in part, on the measured leakage impedance, e.g., as shown at block 208 of FIG. 2, may include RF generator 102, or processor 114 of RF generator 102, disabling RF ablation therapy from being applied to a patient, e.g., a patient represented by ablation impedance 314 in FIG. 3 or section 414 in FIGS. 4A and 4B. For example, in some embodiments, RF ablation therapy may be disabled when the leakage impedance is less than, or equal to, a first threshold impedance. In some embodiments, the leakage impedance being less than, or equal to, the first threshold impedance may indicate that there is excessive leakage current in the RF ablation system. According to some embodiments, the first threshold impedance may be a threshold impedance value associated with an RF ablation system or RF generator, such as RF ablation system 100 or RF generator 102. For example, in some embodiments, the first threshold impedance may be a pre-determined threshold impedance value associated with an RF ablation system or RF generator, such as RF ablation system 100 or RF generator 102. The first threshold may be set in hardware or software. In additional embodiments, the first threshold impedance may be determined based on one or more impedance measurements of RF ablation system 100 or RF generator 102 that are performed by RF generator 102, or processor 114 of RF generator 102. In some embodiments, RF generator 102, or processor 114 of RF generator 102, may perform the one or more impedance measurements before a start of RF ablation therapy. In additional embodiments, RF generator 102, or processor 114 of RF generator 102, may perform the one or more impedance measurements after RF ablation therapy has already started, e.g., while RF ablation therapy is in progress or has not been terminated.

In some embodiments, RF ablation therapy may be disabled when a difference between the leakage impedance and a reference impedance is greater than, or equal to, a second threshold impedance. In some embodiments, the difference between the leakage impedance and the reference impedance being greater than, or equal to, the second threshold impedance may indicate that there is excessive leakage current in the RF ablation system. According to some embodiments, the second threshold impedance and/or the reference impedance may be impedance values associated with an RF ablation system or RF generator, such as RF ablation system 100 or RF generator 102. For example, in some embodiments, the second threshold impedance and/or the reference impedance may be pre-determined impedance values associated with an RF ablation system or RF generator, such as RF ablation system 100 or RF generator 102. The second threshold and/or the reference impedance value may be set in hardware or software. In additional embodiments, the second threshold impedance and/or the reference impedance may be determined based on one or more impedance measurements of RF ablation system 100 or RF generator 102 that are performed by RF generator 102, or processor 114 of RF generator 102. In some embodiments, RF generator 102, or processor 114 of RF generator 102, may perform the one or more impedance measurements before a start of RF ablation therapy. In additional embodiments, RF generator 102, or processor 114 of RF generator 102, may perform the one or more impedance measurements after RF ablation therapy has already started, e.g., while RF ablation therapy is in progress or has not been terminated.

According to some embodiments, an RF generator 102, or processor 114 of RF generator 102, may disable RF ablation therapy when at least one of the foregoing conditions is met. For example, in some embodiments, an RF generator 102, or processor 114 of RF generator 102, may disable RF ablation therapy when at least one of: the leakage impedance is less than, or equal to, the first threshold impedance; or the difference between the leakage impedance and the reference impedance is greater than the second threshold impedance.

In some embodiments, operations disclosed herein with respect to impedance may also be readily performed with respect to current. For example, as disclosed previously, leakage current within an RF ablation system 300 and leakage impedance within the RF ablation system 300 may be related to each other. Therefore, in FIGS. 3, 4A, and 4B, the total leakage current may be measured from the total leakage impedance. For example, in the embodiment of FIG. 3, the total leakage current may be determined by applying a voltage to active electrode 308 while the electrical return path 305 is disabled and measuring the total impedance observed by electrical source 306 of the RF ablation system 300. That resulting impedance may be the leakage impedance, and the total leakage current may be determined by dividing that leakage impedance from the voltage applied to active electrode 308 by electrical source 306.

In some embodiments, an RF generator 102, or processor 114 of RF generator 102, may be configured to measure a leakage current while the electrical return path 305 is disabled and an electrical signal is applied to the active electrode 308, such as an electrode located at a tip of a cannula. Similarly, in some embodiments, an RF generator 102, or processor 114 of RF generator 102, may be configured to measure a leakage current while the electrical return path 405 is disabled and an electrical signal is applied to the active electrode 408, such as an electrode located at a tip of a cannula. According to some embodiments, in FIG. 4B, the total leakage current may be measured from the total leakage impedance. For example, the total leakage current may be determined by applying a voltage to active electrode 408 while the electrical return path 405 is disabled and measuring the total impedance observed by electrical source 406. That resulting impedance may be the leakage impedance, and the total leakage current may be determined by dividing that leakage impedance from the voltage applied to active electrode 408 by electrical source 406.

In some embodiments, an RF generator 102, or processor 114 of RF generator 102, may be further configured to control RF ablation therapy based, at least in part, on the measured leakage current. According to some embodiments, an RF generator 102, or processor 114 of RF generator 102, controlling RF ablation therapy based, at least in part, on the measured leakage current may include RF generator 102, or processor 114 of RF generator 102, disabling RF ablation therapy from being applied to a patient, e.g., a patient represented by ablation impedance 314 in FIG. 3 or section 414 in FIGS. 4A and 4B. For example, in some embodiments, RF ablation therapy may be disabled when the leakage current is greater than, or equal to, a first threshold current. According to some embodiments, the first threshold current may be a threshold current value associated with an RF ablation system or RF generator, such as RF ablation system 100 or RF generator 102. For example, in some embodiments, the first threshold current may be a pre-determined threshold current value associated with an RF ablation system or RF generator, such as RF ablation system 100 or RF generator 102. The first threshold may be set in hardware or software. In additional embodiments, the first threshold current may be determined based on one or more current measurements of RF ablation system 100 or RF generator 102 that are performed by RF generator 102, or processor 114 of RF generator 102. In some embodiments, RF generator 102, or processor 114 of RF generator 102, may perform the one or more current measurements before a start of RF ablation therapy. In additional embodiments, RF generator 102, or processor 114 of RF generator 102, may perform the one or more current measurements after RF ablation therapy has already started, e.g., while RF ablation therapy is in progress or has not been terminated.

In some embodiments, RF ablation therapy may be disabled when a difference between the leakage current and a reference current is greater than, or equal to, a second threshold current. According to some embodiments, the second threshold current and/or the reference current may be current values associated with an RF ablation system or RF generator, such as RF ablation system 100 or RF generator 102. For example, in some embodiments, the second threshold current and/or the reference current may be pre-determined current values associated with an RF ablation system or RF generator, such as RF ablation system 100 or RF generator 102. The second threshold and/or the reference current may be set in hardware or software. In additional embodiments, the second threshold current and/or the reference current may be determined based on one or more current measurements of RF ablation system 100 or RF generator 102 that are performed by RF generator 102, or processor 114 of RF generator 102. In some embodiments, RF generator 102, or processor 114 of RF generator 102, may perform the one or more current measurements before a start of RF ablation therapy. In additional embodiments, RF generator 102, or processor 114 of RF generator 102, may perform the one or more current measurements after RF ablation therapy has already started, e.g., while RF ablation therapy is in progress or has not been terminated.

According to some embodiments, an RF generator 102, or processor 114 of RF generator 102, may disable RF ablation therapy when at least one of the foregoing conditions is met. For example, in some embodiments, an RF generator 102, or processor 114 of RF generator 102, may disable RF ablation therapy when at least one of: the leakage current is greater than, or equal to, the first threshold current; or the difference between the leakage current and the reference current is greater than the second threshold current.

In some embodiments, when leakage impedance and/or leakage current is measured may vary. For example, in some embodiments, the leakage impedance and/or leakage current may be measured before a start of RF ablation therapy. In additional embodiments, the leakage impedance and/or leakage current may be measured after RF ablation therapy has already started, e.g., while RF ablation therapy is in progress or has not been terminated. For example, the leakage impedance and/or leakage current may be measured periodically after RF ablation therapy has started, is in progress, and/or has not been terminated. Accordingly, in some embodiments, an RF generator 102, or processor 114 of RF generator 102, may be configured to measure the leakage impedance and/or leakage current at least one of: before a start of RF ablation therapy; or after RF ablation therapy has started.

According to some embodiments, RF ablation therapy may be disabled in a variety of ways. For example, in some embodiments, an RF generator 102, or processor 114 of RF generator 102, disabling RF ablation therapy may include the RF generator 102, or processor 114 of RF generator 102, preventing a start of RF ablation therapy. In additional embodiments, an RF generator 102, or processor 114 of RF generator 102, disabling RF ablation therapy may include the RF generator 102, or processor 114 of RF generator 102, preventing additional RF ablation therapy after RF ablation therapy has started. For example, additional RF ablation therapy may be prevented from being applied to a patient after RF ablation therapy has started for the patient.

It is noted that one or more blocks, operations, and/or components described with reference to some Figures may be combined with one or more blocks, operations, and/or components described with reference to other Figures. For example, one or more blocks, operations, and/or components of FIGS. 3 and/or 4 may be combined with one or more blocks, operations, and/or components of FIGS. 1 and/or 2. As another example, one or more blocks, operations, and/or components associated with FIGS. 1 and/or 3 may be combined with one or more blocks, operations, and/or components associated with FIGS. 2 and/or 4.

Components, the functional blocks, and modules described herein (e.g., the components, functional blocks, and modules in FIG. 1) may comprise processors, electronics devices, hardware devices, electronics components, logical circuits, memories, software codes, firmware codes, etc., or any combination thereof. In addition, features discussed herein may be implemented via specialized processor circuitry, via executable instructions, and/or combinations thereof.

Those of skill would further appreciate that the various illustrative logical blocks, modules, circuits, and algorithm steps (e.g., the logical blocks in FIG. 2) described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), hard disk, solid state disk, and blu-ray disc where disks usually reproduce data magnetically, while discs reproduce data optically with lasers.

Combinations of the above should also be included within the scope of computer-readable media.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C) or any of these in any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A method for controlling a radio-frequency (RF) ablation system, comprising:
   disabling an electrical return path from a patient to a ground terminal;
   applying an electrical signal to an electrode that is positioned to be in proximity to target tissue of the patient;
   measuring a leakage impedance while the electrical return path is disabled and the electrical signal is applied to the electrode; and
   controlling RF ablation therapy based, at least in part, on the measured leakage impedance.

2. The method of claim 1, wherein the controlling of the RF ablation therapy based, at least in part, on the measured leakage impedance includes disabling RF ablation therapy when the leakage impedance is less than a first threshold impedance.

3. The method of claim 1, wherein the controlling of the RF ablation therapy based, at least in part, on the measured leakage impedance includes disabling RF ablation therapy when a difference between the leakage impedance and a reference impedance is greater than a second threshold impedance.

4. The method of claim 1, wherein the controlling of the RF ablation therapy based, at least in part, on the measured leakage impedance includes disabling RF ablation therapy, and wherein disabling RF ablation therapy includes preventing a start of RF ablation therapy.

5. The method of claim 1, wherein the controlling of the RF ablation therapy based, at least in part, on the measured leakage impedance includes disabling RF ablation therapy, and wherein disabling RF ablation therapy includes preventing additional RF ablation therapy after RF ablation therapy has started.

6. The method of claim 1, wherein the leakage impedance includes impedance observed by an electrical source of the RF ablation system when the electrical return path is disabled.

7. The method of claim 1, wherein the leakage impedance is measured at least one of:
   before a start of RF ablation therapy; or
   after RF ablation therapy has started.

8. The method of claim 1, wherein the leakage impedance is measured periodically after RF ablation therapy has started.

* * * * *